(12) United States Patent
Knutson et al.

(10) Patent No.: US 9,448,158 B2
(45) Date of Patent: Sep. 20, 2016

(54) LIGHTGUIDES TO SIMPLIFY TOTAL EMISSION DETECTION FOR MULTIPHOTON MICROSCOPY

(75) Inventors: Jay R. Knutson, Kensington, MD (US); Christian A. Combs, Bethesda, MD (US); Robert S. Balaban, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 120 days.

(21) Appl. No.: 13/983,534

(22) PCT Filed: Feb. 3, 2012

(86) PCT No.: PCT/US2012/023838
§ 371 (c)(1),
(2), (4) Date: Aug. 2, 2013

(87) PCT Pub. No.: WO2012/106641
PCT Pub. Date: Aug. 9, 2012

(65) Prior Publication Data
US 2013/0308126 A1    Nov. 21, 2013

Related U.S. Application Data

(60) Provisional application No. 61/439,616, filed on Feb. 4, 2011.

(51) Int. Cl.
*G01N 21/01*     (2006.01)
*G01N 21/64*     (2006.01)
(Continued)

(52) U.S. Cl.
CPC .......... *G01N 21/01* (2013.01); *G01N 21/6458* (2013.01); *G02B 6/241* (2013.01); *G02B 21/16* (2013.01); *G02B 21/26* (2013.01)

(58) Field of Classification Search
CPC .... G02B 6/00; G02B 6/0001; G02B 6/0011; G02B 6/002; G02B 6/0021; G02B 6/0033–6/0048; G02B 6/0058; G02B 6/0075–6/0076; G02B 6/0091; G02B 6/0096; G02B 21/06; G02B 21/16; G02B 21/24; G02B 21/26; G02B 21/34; G01N 21/01; G01N 21/64; G01N 21/6458; G01N 2021/0106–2021/0112
USPC ......... 385/129–132, 133, 146; 359/362, 368, 359/385–391, 398, 850, 853, 855, 857; 356/244, 246; 435/288.3–288.5, 288.7, 435/305.1–305.4; 206/456
See application file for complete search history.

(56) References Cited

U.S. PATENT DOCUMENTS 4,189,236 A * 2/1980 Hogg et al. ................... 356/317
4,260,219 A * 4/1981 Greubel et al. ............... 136/247
(Continued)

FOREIGN PATENT DOCUMENTS

JP     11-173946     7/1999

OTHER PUBLICATIONS

Engelbrecht et al., "Enhanced fluorescence signal in nonlinear microscopy through supplementary fiber-optic light collection," *Optics Express* 17:6421-6435 (Apr. 2, 2009).
(Continued)

*Primary Examiner* — Stephone B Allen
*Assistant Examiner* — Adam W Booher
(74) *Attorney, Agent, or Firm* — Klarquist Sparkman, LLP (57) ABSTRACT

Light collectors for fluorescence microscopy include slab light guides having a specimen volume such as a specimen well configured to retain a specimen. The specimen volume is bounded by a surface of the slab light guide that permits laterally propagating fluorescence to enter the slab light guide and propagate toward a detection or imaging system. Typically, the slab light guide has an elliptical perimeter and the sample volume is situated at a first focus of the elliptical perimeter. A reflector such as a conical reflector is situated at the second focus so as to direct the collected fluorescence to exit the slab light guide.

27 Claims, 10 Drawing Sheets

(51) Int. Cl.
*G02B 21/16* (2006.01)
*G02B 6/24* (2006.01)
*G02B 21/26* (2006.01)

(56) References Cited

U.S. PATENT DOCUMENTS

| | | | |
|---|---|---|---|
| 4,723,825 A * | 2/1988 | Herold | 433/141 |
| 5,801,881 A | 9/1998 | Lanni et al. | |
| 6,980,374 B1 | 12/2005 | Schlesinger | |
| 7,380,962 B2 | 6/2008 | Chaves et al. | |
| 7,488,955 B2 | 2/2009 | Okada et al. | |
| 7,667,210 B2 | 2/2010 | Balaban et al. | |
| 2001/0028497 A1 | 10/2001 | Uhl | |
| 2005/0043636 A1 | 2/2005 | Gaeta et al. | |
| 2006/0002101 A1 * | 1/2006 | Wheatley et al. | 362/84 |
| 2008/0063345 A1 | 3/2008 | Balaban et al. | |
| 2008/0278460 A1 | 11/2008 | Arnett et al. | |
| 2010/0085750 A1 | 4/2010 | Van Ostrand et al. | |

OTHER PUBLICATIONS

Engelbrecht et al., "Miniaturized selective plane illumination microscopy for high-contrast in vivo fluorescence imaging," Opt. Letters 35:1413-1415 (Apr. 2, 2009).

Engelbrecht et al., "Ultra-compact fiber-optic two-photon microscope for functional fluorescence imaging in vivo," Opt. Express 16:5556-5564 (Apr. 14, 2008).

International Search Report and Written Opinion from International Application No. PCT/US2012/023838, dated Jul. 27, 2012, 9 pages.

McMullen et al., "Enhancing collection efficiency in large field of view multiphoton microscopy," Journal of Microscopy, No. doi:10.1111/j.1365-2818 (2010).

Mendes and Saavedra, "On probing molecular monolayers: a spectroscopic optical waveguide approach of ultra-sensitivity," *Optics Express* 4:449-456 (1999).

Schelb et al. "Monolithical Integration of UV-induced Optical Polymer Waveguides for Fluorescence Applications in Biological Sciences," 2010 Conference on Lasers and Electro-Optics, 2 pages.

* cited by examiner

LIGHTGUIDES TO SIMPLIFY TOTAL EMISSION DETECTION FOR MULTIPHOTON MICROSCOPY

CROSS REFERENCE TO RELATED APPLICATIONS

This is the U.S. National Stage of International Application No. PCT/US2012/023838, filed Feb. 3, 2012, which was published in English under PCT Article 21(2), which in turn claims the benefit of U.S. Provisional Application No. 61/439,616, filed Feb. 4, 2011. The provisional application is incorporated herein in its entirety.

ACKNOWLEDGMENT OF GOVERNMENT SUPPORT

This invention was made by an agency of the United States Government or under a contract with an agency of the United States Government. The name of the U.S. Government agency is: the Department of Health and Human Services, National Institutes of Health.

FIELD OF THE DISCLOSURE

The disclosure pertains to light collection optics for multiphoton microscopy.

BACKGROUND

Traditional microscopy permits the examination of biological structures using a variety of techniques based on light transmission, reflection, polarization, luminescence, and scattering. By combining these methods with staining protocols, clinicians and researchers both acquire powerful tools to evaluate biological and other specimens.

With the advent of intense laser light sources, it has become practical to provide specimen images based on both linear and non-linear effects obtained in response to an intense optical beam. For example, with such intense beams, a specimen illuminated by a laser at a first wavelength can produce radiation at a second, third, fourth, or other harmonic of the first wavelength, or at some other wavelengths. In so-called multiphoton microscopy a specimen emits a light flux in response to a light flux exciting a material via a multiphoton process (usually multiphoton absorbance leading to luminescence, e.g., fluorescence or phosphorescence). In fluorescence microscopy, fluorescence produced in a specimen in response to a stimulating light flux is used to form a specimen image. In both fluorescence microscopy and other multiphoton microscopies, there are methods that relay and focus emitted light flux to produce an image directly; usually, however, the image is formed by quantifying the emitted light flux that is localized by scanning the stimulating light flux across the specimen.

Generally, light produced by multiphoton emission (e.g., fluorescence) is relatively weak, and high optical intensities are needed to produce satisfactory emitted light levels. Thus, when nonlinear effects or fluorescence are used in microscopic evaluations, only weak optical signals are often available for imaging and these optical signals must be detected in the presence of much stronger illumination beams. In addition, in order to increase multiphoton emission or fluorescence, increased illumination intensities are needed. Unfortunately, increased illumination beam intensity is associated with specimen damage or degradation such as specimen bleaching. Thus, even though increased illumination intensity can produce increased nonlinear emission and/or fluorescence, the associated damage reduces useful observation times. Accordingly, efficient collection of nonlinear emission beyond that which is available with conventional high numerical aperture objective lenses is needed.

Existing multiphoton microscopy systems may be enhanced by combinations of minors and lenses arranged to collect multiphoton fluorescence, either the component that propagates generally in the direction of the stimulus beam and is transmitted by a specimen ("trans light") or the multiphoton fluorescence that is propagates backwards toward the excitation beam ("epi" light). One representative system is described in Balaban, Combs, and Knutson, U.S. Pat. No. 7,667,210, that is incorporated herein by reference. While such systems can be practical and permit improved light detection with respect to conventional systems, further improvements are needed.

SUMMARY OF THE DISCLOSURE

Light collectors for a fluorescence microscope include a slab light guide defined by first and second opposing surfaces, the slab light guide including a relief volume situated between the opposing surfaces and configured to receive a specimen for irradiation by an excitation beam. The relief volume is bounded by at least one transmissive optical surface that passes received fluorescence from the specimen in the relief volume into the slab light guide. The slab light guide includes a perimeter surface substantially perpendicular to a slab plane configured to reflect the received fluorescence propagating within the slab light guide to an output surface. In some examples, the opposing surfaces of the slab light guide are tilted with respect to each other so as to define a tapered slab light guide. In alternative examples, the opposing surfaces of the slab light guide are substantially parallel. In some embodiments, the perimeter surface of the slab light guide is elliptical and the relief volume is situated at one focus of the ellipse. In additional examples, a reflector is situated between the opposing surfaces that define the slab light guide and at the second focus of the elliptical perimeter surface so as to direct fluorescence propagating within the slab light guide so as to exit the slab light guide through at least one transmissive portion of the opposing surfaces. In further examples, the reflector has a conical reflective surface. In still additional examples, a tapered light guide section is configured to direct the fluorescence propagating within the slab light guide to an output surface. In some examples, the perimeter of the slab light guide includes a parabolic section. In other representative examples, a propagation axis associated with the tapered light guide section includes a portion that is substantially perpendicular to at least one of the opposing surfaces.

Apparatus comprise a first slab light guide having a specimen volume; and a reflective surface situated between exterior surfaces of the first slab light guide. A perimeter surface of the first slab light guide is configured so as to direct light flux received into the slab volume from the specimen volume to the reflective surface. The reflective surface is configured to reflect the received light flux so as to exit the first slab light guide. In additional examples, the perimeter surface of the first slab light guide includes an elliptical section and the specimen volume and reflective surface are situated at first and second focal points of the elliptical section. In further examples, a second slab light guide that includes first and second reflective surfaces at least partially situated between exterior surfaces of the second slab light guide is and situated with respect to the first slab light guide so that a light flux transmitted from the specimen volume of the first slab light guide is at least partially received by the first reflective surface and directed by the first reflective surface and the second slab light guide to the second reflective surface of the second slab light guide. In some examples, the second slab light guide has a perimeter corresponding to an elliptical section, and the first and second reflective surfaces are defined by conical or complex conic (e.g., cones with walls shaped to correspond to a section of a parabola or other two dimensional curve rotated about a cone axis normal to the slab) surfaces at first and/or second foci of the elliptical section. In further examples, a first axis that extends between the first and second focal points of the first slab light guide and a second axis that extends between the first and second focal points of the second slab light guide define an angle of between 10 degrees and 180 degrees. In further examples, the perimeter surface of the first slab light guide includes a tapered portion and an elliptical portion.

Methods include exposing a specimen to an incident beam so as to produce fluorescence from the specimen and collecting at least a portion of laterally propagating fluorescence with a first slab light guide so as to propagate within the first slab light guide to direct the fluorescence to a detection system. In some examples, "trans" light is additionally diverted by a (complex conic) reflector within a second slab to travel laterally within the second slab and be diverted by another reflector (or refracted by a curved surface) to a detector outside the guide. In other examples, at least a portion of the laterally propagating fluorescence is directed out of the slab light guide with a reflective surface situated within the slab light guide. In typical examples, the perimeter of the slab light guide includes a parabolic or an elliptical section. In further embodiments, at least a portion of the collected lateral fluorescence is directed to an output surface with a tapered light guide.

These and other aspects and features of the disclosed technology are described below with reference to the accompanying drawings.

DETAILED DESCRIPTION OF SEVERAL EMBODIMENTS

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

Methods and apparatus are provided that are typically based on one or more slab light guides that are arranged to receive and direct a "trans" component, an "epi" component, or a lateral (e.g., quasi-equatorial) component of a light flux received from a specimen. As used herein, an incident light flux directed to a specimen can be referred to as an illumination light flux, an excitation or irradiation light flux, or a stimulus light flux that are generally suitable for visible imaging (including direct viewing in a microscope), imaging at one or more wavelength ranges at which the human eye is not appreciably sensitive (for example, imaging with near infrared or ultraviolet wavelengths), or to produce fluorescence or multiphoton emission at the specimen, respectively. It will be appreciated that in many practical examples, an incident light flux includes light flux components for a variety of purposes. For example, an incident light flux can include a component suitable for direct image viewing and a component configured to produce multiphoton emission. These components can be distinct and provided by distinct sources, or a single light flux from a single source can be used. In some examples, an emission light flux is any light flux that is received from a specimen, whether transmission or reflection of a stimulus light flux or other light flux incident to the specimen, or to fluorescence or other light flux produced at the specimen. In some cases, light can be generated by chemiluminescence, electrical stimulation, or otherwise produced without optical stimulation An incident light flux that propagates along an axis and received by a specimen can be associated with a "trans" component that propagates in a direction that is along the axis, and generally within a solid angle defined by an angle of up to about 70 degrees with respect to the axis. However, trans components can be associated with greater or smaller angles based on effective numerical apertures of optical elements used to capture this light flux. An incident light flux that propagates along an axis to a specimen can be associated with an "epi" component that propagates in a direction that is along the axis but opposite a direction of incidence, and generally propagates within a solid angle defined by an angle of up to about 70 degrees with respect to the axis. However, epi components can be associated with greater or smaller angles based on effective numerical apertures of optical elements used to capture this light flux. An incident light flux that propagates along an axis to a specimen can also be associated with a lateral emission component that propagates in a direction that is perpendicular to the incidence axis, or a direction that is at an angle of ±40 degrees with respect to a perpendicular axis, but may include an angle of up to about 80 degrees with respect to the perpendicular axis if trans and epi collection optics have low numerical apertures. Thus, the portion not ascribed to lateral propagation can be divided into trans and epi light fluxes. In addition, it will be appreciated that an axis of propagating or other optical axis generally includes a straight line portion, but such axes can be bent, folded, or otherwise deviate from straight line using mirrors, prisms, lenses or other optical components.

Trans, epi, and lateral light fluxes can include portions corresponding to transmission, reflection, and scattering of an incident light flux, or portions associated with single photon or multiphoton excited fluorescence (or other emissions) in the specimen that arise in response to a stimulus beam. In some examples, these fluxes include portions of the incident light flux as well as fluorescence (or other emission) generated in response to the incident light flux. The combined fluxes can be directed to common detection system or one or both can be delivered to respective detection systems. In some examples, a component produced by multiphoton fluorescence is directed to a detection system and a co-propagating component associated with the incident light flux is attenuated.

As used herein, a conical reflector can be provided as a solid section of a cone that can include a cone apex or can be a truncated section. Such a solid section can be referred to as an axicon, and can be formed of an optical glass, fused silica, or other convenient transmissive media. Alternatively, sections of hollow conical shells having a reflective surface that is defined by a dielectric, metallic, or other reflective coating can be used. Cones having circular cross-sections are typically preferred, but cones having elliptical or other curved cross-sections can be used, and in some examples, polygonal cross-sections can be used. In still other examples, an axicon can be formed as conical relief volume in a solid material, such as a conical shaped void in a glass or fused silica slab light guide. In some examples, conical reflectors are defined by surfaces of revolution about an axis.

As used herein, "optical flux" or "light flux" refers to propagating electromagnetic radiation in a wavelength range of between about 10 nm and 500 µm, although in many practical examples, a wavelength range of between about 200 nm and 2 µm is used. While an optical flux can be collimated, collimation is not required and optical beams can be converging or diverging, and need not be circularly symmetric.

Disclosed herein are methods and apparatus that can provide convenient collection of multiphoton excited fluorescence and direction of the collected fluorescence to a detector. In some examples, one or more slab light guides are defined in a sheet of a material that is optically transparent at multi-photon emission wavelengths, and a specimen is situated in a cavity or aperture in the optically transparent sheet. The walls of the specimen aperture are configured to collect and transmit multiphoton fluorescence (or other light flux from the specimen) so that the collected light propagates within the slab light guide. The nearly planar slab light guide can be elliptical in shape and the specimen aperture situated at a first focus of the ellipse. A conical reflector can be situated at a second focus. Thus, captured fluorescence propagating within the sheet is directed by reflection at slab walls to the conical reflector at the second focus. After reflection by the conical reflector, the fluorescence is directed out of the slab light guide to a detection system. The surfaces of the sheet (including the sheet perimeter) can be provided with dielectric or metallic reflective coatings to increase the efficiency with which the captured fluorescence can be delivered to the detection system. In the disclosed examples, a slab light guide is generally defined is a uniform or tapered sheet of one or more transmissive materials such as glass, fused silica, a plastic such as methacrylates or styrene, or other materials. Materials can be chosen to either attenuate or convert a light flux with one range of wavelengths to another. In additional example, slab light guides can be defined by reflective surfaces that define a hollow structure.

Figure 1A:
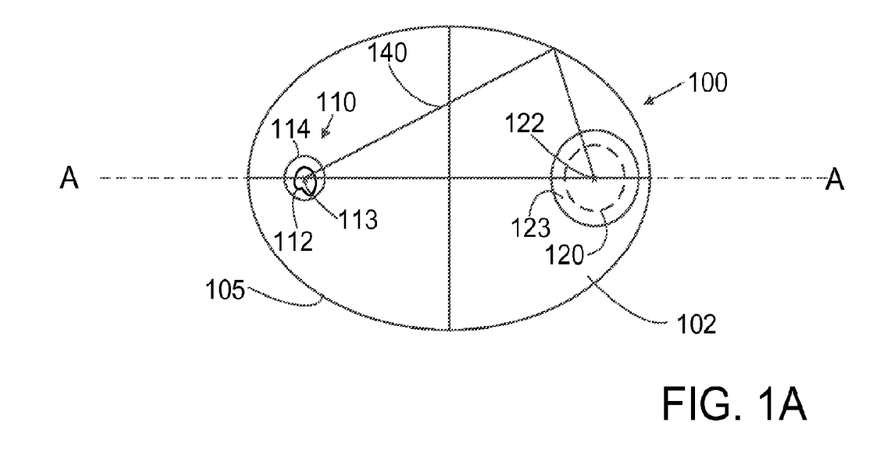
FIG. 1A is a plan view of a representative slab light guide light collector.
Figure 1B:
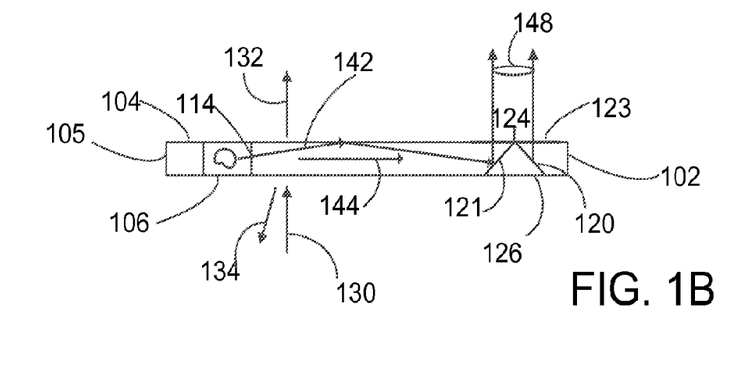
FIG. 1B is a sectional view of the slab light guide light collector of FIG. 1A taken along a line AA shown in FIG. 1A.

With reference to FIGS. 1A-1B, a slab light guide light collector 100 includes an elliptical slab 102 of an optically transparent material having a reflective top surface 104, a reflective bottom surface 106, and a reflective perimeter surface 105. As noted above, suitable materials for a solid slab light guide include, for example, glass, fused silica, and transmissive plastics. The top surface 104 and the bottom surface 106 can optimally be provided with metallic or dielectric coatings to increase surface reflectivity at some wavelengths and/or increase surface transmission at some wavelengths, or the surfaces 104, 106 can be uncoated and have reflectivities associated with an index of refraction difference. In the example of FIGS. 1A-1B, the surfaces 104, 106 are generally substantially planar and appear smooth.

The elliptical slab 102 includes an aperture 110 within which a specimen 112 can be situated. The aperture 110 typically has a circular cross-section and is approximately centered on a first focus 113 of the elliptical slab. An aperture side wall 114 is substantially smooth and/or optically polished so that light received at the aperture wall 114 from the specimen 112 is coupled into the elliptical slab 102. The aperture wall 114 can be provided with an anti-reflection coating if desired. The aperture walls may be cylindrical or the walls can be relieved or curved in aspect to enhance coupling or facilitate approach of other optical components to the specimen. The aperture 110 can extend though the entire thickness of the slab 102, or can extend partially through the slab 102 so as to define a well in which the specimen can be retained. If the slab 102 includes a specimen well, an index matching liquid can be provided.

A conical reflector 120 having a conical reflective surface 121 is situated at a second focus 122 of the slab 102. The surface 121 can also be defined by a conical void in the slab 102. As shown in FIGS. 1A-1B, the conical reflector 120 has an apex 124 that is situated at (or nearly at) the top surface 104 and a base surface 126 that is substantially coplanar with the bottom surface 106. In some examples, the surface 104 is provided with a reflective coating such as a metallic or dielectric coating, and a transmissive aperture 123 is provided at the conical reflector 120 on the top surface 104. If desired, the aperture 123 can be provided with an anti-reflection coating. As shown in FIG. 1A, the aperture 123 is somewhat larger than a maximum diameter of the conical reflector 120 and is centered about the conical reflector 120.

In typical applications, stimulus beam 130 is directed to the specimen 112, and a light flux is produced in response at the specimen 112 by scattering, fluorescence, multiphoton excited emission, structure excitation, or other process. In some cases, the produced light flux propagates over a wide range of solid angles. A transmitted light flux 132 exits the specimen 112 and the slab 102 and a reflected, back emitted, or backscattered light flux 134 exits the slab 102. The transmitted and reflected light fluxes 132, 134 can be directed to one or more objective lenses or other optical elements, collected, and processed to form corresponding images of the specimen. For convenient illustration, the associated optical elements are not shown in FIGS. 1A-1B, but examples thereof are described in Balaban et al., U.S. Pat. No. 7,667,210, which is incorporated herein by reference.

At least some portion of the light flux produced in response to the stimulus beam propagates so as to be directed to the aperture wall 114. This flux is generally coupled into the slab 102 and can be confined in the slab 102 by total internal reflection at the top surface 104 and the bottom surface 106 (or reflective coatings at these surfaces). The specimen 112 is located at (or near) the first focus 113 of the elliptical slab 102 so that this flux propagates within the elliptical slab so as to be directed toward the second focus. FIG. 1A illustrates propagation from the specimen 112 along a representative ray direction 140 to the conical reflector 120. Other portions of the flux propagating along other ray directions within the slab 102 from the specimen 112 similarly extend to the conical reflector 120. FIG. 1B illustrates propagation from the specimen along additional representative ray directions 142, 144 to the conical reflector 120. Propagation along ray direction 142 includes reflection at the top surface 104. The portion of the light flux from the specimen 112 that is received by the conical reflector 120 is reflected to form an output beam 148 that can be directed to a detection system or otherwise processed to aid in specimen evaluation.

Figure 2:
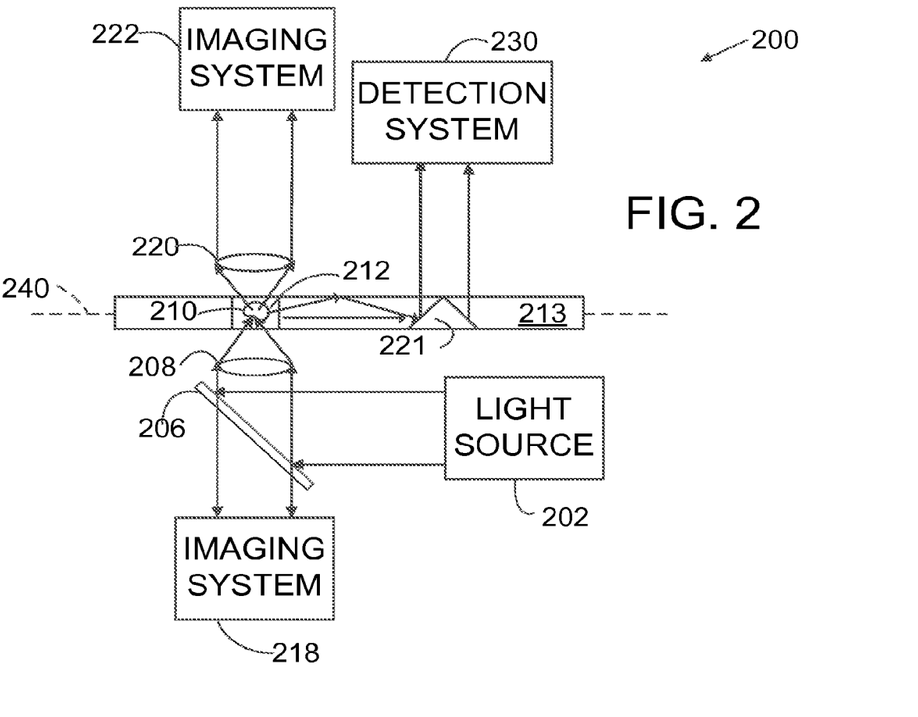
FIG. 2 is a schematic diagram of an optical system configured for specimen evaluation based on transmitted, reflected, and laterally directed light fluxes produced in response to one or more excitation or illumination beams.

FIG. 2 is a schematic diagram of an imaging system 200 that includes a slab light guide based light collector such as illustrated in FIGS. 1A-1B. A light source 202 is configured to direct an illumination beam to a reflective dichroic filter 206 that in turn directs the illumination beam to a first objective 208 that converges the illumination beam at a specimen 210 that is situated at a specimen chamber 212 in a slab light guide 213. While the light source 202 is shown as a single component, the light source can provide illumination in one or more wavelength ranges to, for example, stimulate multiphoton emission and/or permit visible imaging. The filter 206 can be configured to reflect a stimulus beam to the specimen 210 and transmit fluorescence or multiphoton emission to an imaging system 218. The filter 206 may also be selected to partially reflect a visible light flux from the light source 202 to the specimen 210 and transmit a reflected portion to the imaging system 218. Imaging systems such as the imaging system 218 can include one or more lenses such as eyepiece lenses to provide images for direct viewing, or can include electronic detection systems based on detector arrays that produce electrical image signals that can be digitized and stored. Additional light sources can be provided in other locations as well. In some cases, the light source can be raster scanned across the specimen and the depth within the specimen can be scanned via movement of the entirety of the objective 208 or focus movement with elements inside the objective 208. The objective 208 is typically a compound lens such as a microscope objective that includes a plurality of lens elements, but is illustrated as a single lens element for convenience. In some examples, reflective objectives can be used, and generally a combination of reflective and refractive optical elements can be used as convenient for a particular application.

A light flux associated with fluorescence, multiphoton emission, or scattering propagates towards the first objective 208 and a second objective 220 as well as portion of a stimulus beam and/or a visible light flux. The combined "epi" light flux can be directed to the imaging system 218 and the combined "trans" light flux can be directed an imaging system 222. The imaging systems 218, 222 can be configured to separate and process different spectral components of the emitted, reflected, and transmitted light fluxes so as to produce images or detect the light fluxes for further processing.

A portion of the light flux associated with fluorescence, multiphoton emission, or scattering propagates from the specimen 210 within the slab light guide 213 and is received by a conical reflector 221 that reflects this portion to a detection system 230. As the specimen 210 and the conical prism 221 are situated at foci of the elliptical slab light guide 213, a light flux propagating from the specimen 210 tends to be focused upon the conical prism 221.

The system of FIG. 2 is based on detection and/or imaging with light reflected (or emitted) generally back towards an illumination source (so-called "epi" detection) as well as light transmitted generally along the direction of propagation of the illumination flux. In addition, portions of a light flux that propagates within a volume that is substantially coplanar with a specimen plane 240 is captured. The entire slab 202 or the specimen 210 can be manipulated to raster scan an image in any of three axes.

Figure 3:
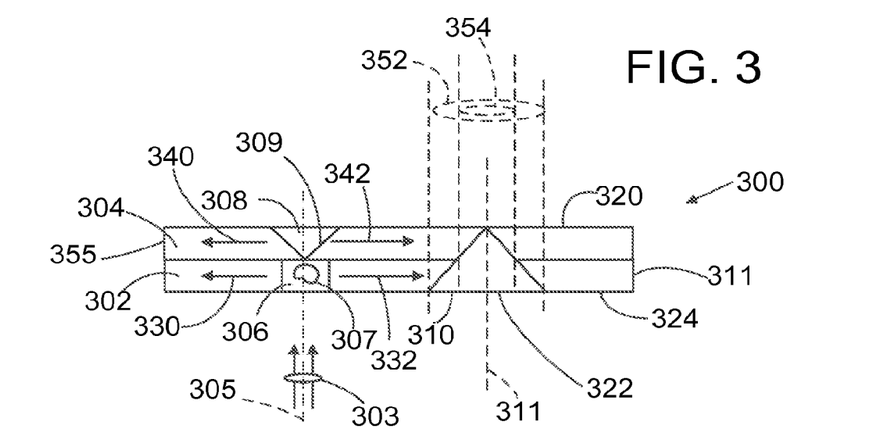
FIG. 3 is a sectional view of a stacked elliptical slab light guides configured to capture transmitted light and laterally directed light.

FIG. 3 illustrates a representative example of a light collector 300 that includes two elliptical slab layers. A first slab layer 302 is configured to collect light propagating approximately parallel to a sample plane that is perpendicular to a propagation axis 305 of an illumination beam 303 and containing a specimen 307. The slab layer 302 includes a recess 306 that is configured to receive the specimen 307 and is situated at a focus of the ellipse that defines a reflective perimeter 311 of the first slab layer 302. In use, the propagation axis 305 typically extends through a focus of the ellipse. The second slab layer 304 includes a conical reflector 308 that is approximately centered on a center of the sample recess 306 along the axis 305 and also at a focus of an elliptical perimeter 355 of the second slab layer 304. As noted above, a conical reflective surface 309 can be provided as a surface of the conical reflector 308 or formed as a wall of a conical recess. A focus of the second slab light guide 304 is also on the axis 305. In some examples, the conical reflective surface 309 is provided by a metallic coating or a dielectric coating. In addition, the reflective surface 309 can have a parabolic, cylindrical, or other curvature.

A second conical reflector 310 is situated along an axis 311 that extends through a focus of the first and second slab layers. An apex of the second conical reflector is substantially coplanar with a surface 320 of the second slab layer 304 and a base surface 322 is substantially coplanar with a surface 324 of the first slab layer 302. Portions of light reflected, scattered, or produced at the specimen directed within the first slab 302 along representative propagation directions 330, 332 so that this light flux arrives at the second conical reflector 310 for reflection along the axis 311 to a detection system or imaging system. Light portions transmitted or scattered so as to exit the sample aperture 306 upward along the axis 305 are reflected by the first conical reflector 308 so as to propagate toward to the second conical reflector 310 for reflection to a detection or imaging system. For example, light portions propagating along representative propagation directions 340, 342 are directed to the second conical reflector 310 by the peripheral surface 355 of the slab layer 304. Thus, as shown in FIG. 3, a "sideways" propagating light flux is guided by the first slab light guide 302 and a "trans" light flux is guided by the second slab light guide 304, and these fluxes generally exit the slabs in beam cross-sections 352, 354, respectively.

Figure 9:
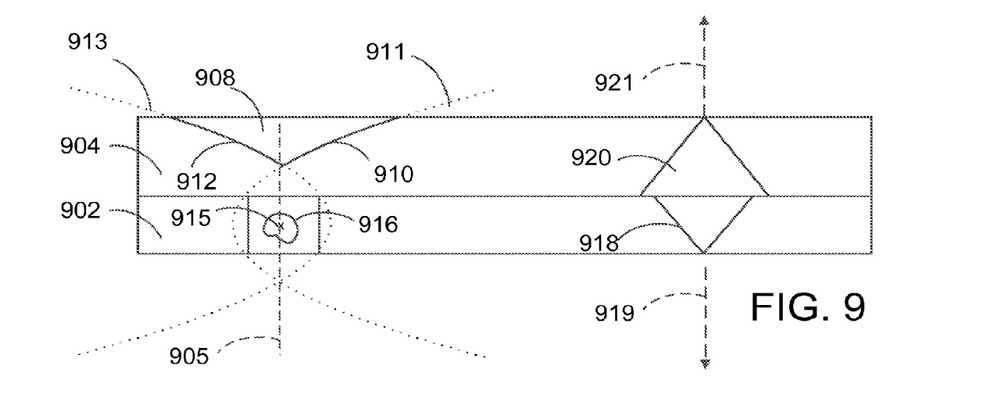
FIG. 9 is a sectional view of a slab light guide that includes a parabolic reflective surface.

An alternative pair of slab light guides is illustrated in FIG. 9. A first slab layer 902 includes a reflector 918 situated to reflect light propagating in the first slab layer 902 along a first axis 919. A second slab layer 904 includes a parabolic profile reflector 908 having rotated parabolic profile reflective surface having surface profiles 910, 912 in the plane of FIG. 9 whose focus 915 (the source of light that will reflect from the parabolic surface to propagate substantially in the plane of the slab layer 904) is on an axis 905 on which a specimen 916 is situated. For purposes of illustration, outlines 911, 913 of a rotated parabola are shown that define the surface portions 910, 912. The second slab 904 also includes a reflector 920 configured to reflect light from the reflector 920 along an axis 921. (A single reflector could be used instead, as shown in FIG. 3.) In other examples, the surfaces 910, 912 could be based on portions of one or more spherical, elliptical, or other complex polygonal surfaces. In addition, as shown in FIG. 9, the reflector 908 need not extend through the entire thickness of the slab 904. In addition, the slabs 902, 904 need not have the same perimeter and can share one focus and not a second.

Figure 4A:
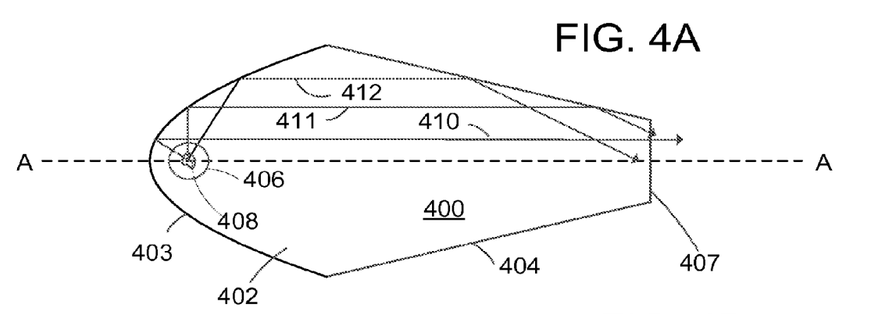
FIGS. 4A-4B are plan and sectional views, respectively, of a slab light guide light collector that includes a parabolic section and a tapered section.
Figure 4B:
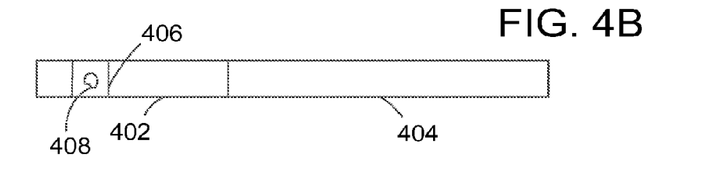

Referring to FIGS. 4A-4B, a slab light guide 400 includes a first section 402 having a parabolic perimeter 403 and a second section 404 that tapers from the parabolic section 402 to an output surface 407. A specimen 408 is situated in a specimen recess 406 that is situated at a focus of the parabolic section 402. Representative propagation paths 410, 411, 412 extend from the specimen 408 to the output surface 407. A detection system can be optically coupled to the output surface 407 to collect, for example, multiphoton fluorescence from the specimen 408. While a parabolic perimeter for the first section 402 can provide superior results, a circular section, an elliptical section, or other curve can be used that directs a light flux from a specimen recess to a collection location.

Figures 5A, 5B:
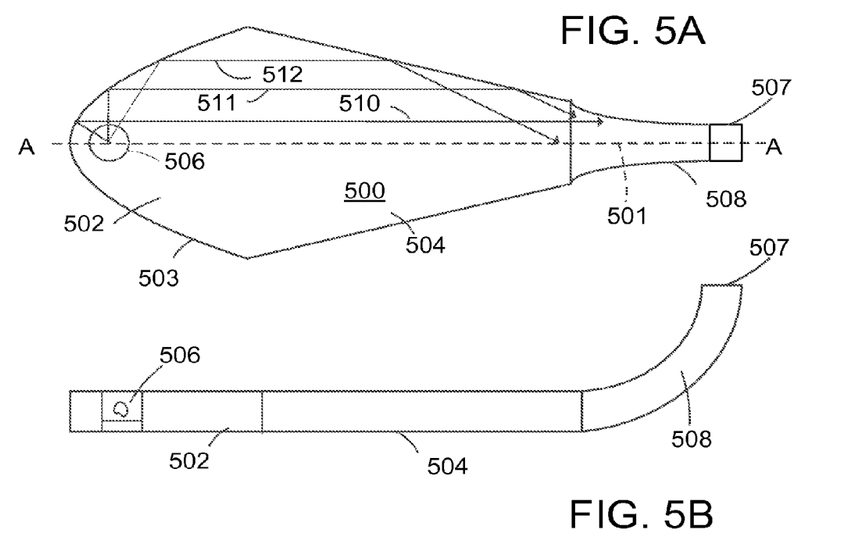
FIGS. 5A-5B are plan and sectional views, respectively, of a slab light guide light collector that includes co-planar parabolic and tapered sections, and a tapered light guide section for coupling to a detection system.

FIGS. 5A-5B illustrate a slab light guide 500 includes a first section 502 having a parabolic perimeter 503 and a second section 504 that tapers from the parabolic section 502 to an output light guide section 508 that terminates at an output surface 507. A specimen recess 506 is situated at a focus of the parabolic section 502. Representative propagation paths 510, 511, 512 extend from the specimen recess 506 to the output light guide section 508. A detection system can be optically coupled to the output surface 507 to collect, for example, multiphoton fluorescence from a specimen. As shown in FIG. 5B, the output light guide section 508 curves out of a plane containing the parabolic section 502 and the tapered section 504. The light guide section 508 can be tapered in along one or more axes to form a tapered slab, a tapered light pipe, or other shape. In FIGS. 5A-5B, the sections 502, 504, 508 are aligned on an axis 501, but in other examples can be arranged on axes that bend or curve as convenient.

Figure 6A:
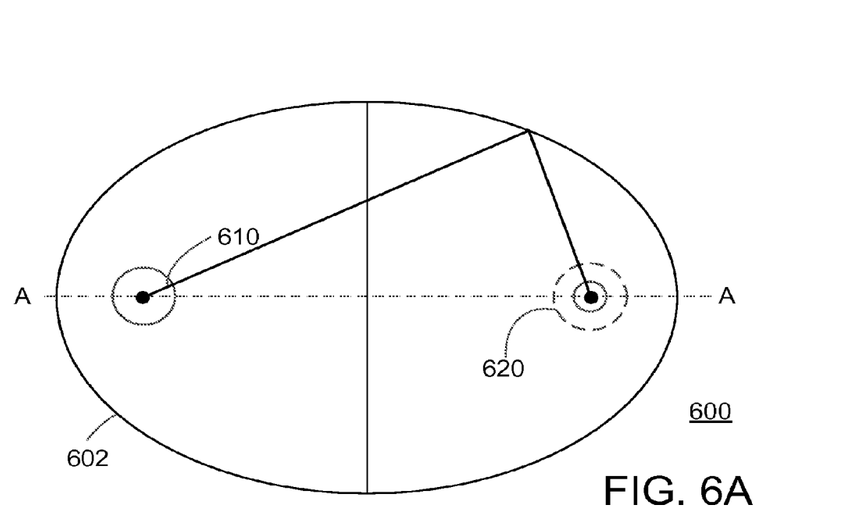
FIGS. 6A-6B are plan and sectional views, respectively, of an elliptical slab light guide light collector having a truncated conical reflector.
Figure 6B:
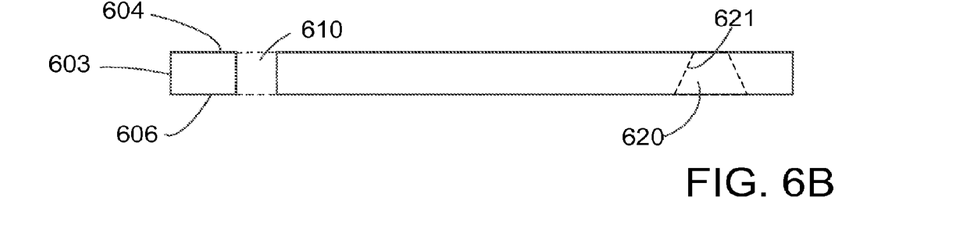

With reference to FIGS. 6A-6B, a slab light guide light collector 600 includes an elliptical slab 602 of an optically transparent material having a reflective top surface 604, a reflective bottom surface 606, and a reflective perimeter surface 603. The elliptical slab 602 includes a specimen aperture 610 within which a specimen can be situated. The aperture 610 typically has a circular cross-section and is approximately centered on a first focus of the elliptical slab. The aperture 610 can extend though the entire thickness of the slab 602, or can extend partially through the slab 602 so as to define a well in which the specimen can be retained.

A truncated conical reflector 620 having a conical reflective surface 621 is situated at a second focus of the slab 602. The surface 621 can also be defined by a truncated conical void in the slab 602. As shown in FIGS. 6A-6B, the conical reflector 620 has a first surface that is situated at (or nearly at) the top surface 604 and a base surface that is substantially coplanar with the bottom surface 606. Reflective coatings on the surface 604 may be removed above 620 or replaced with dichroic or antireflection coatings.

Figure 7:
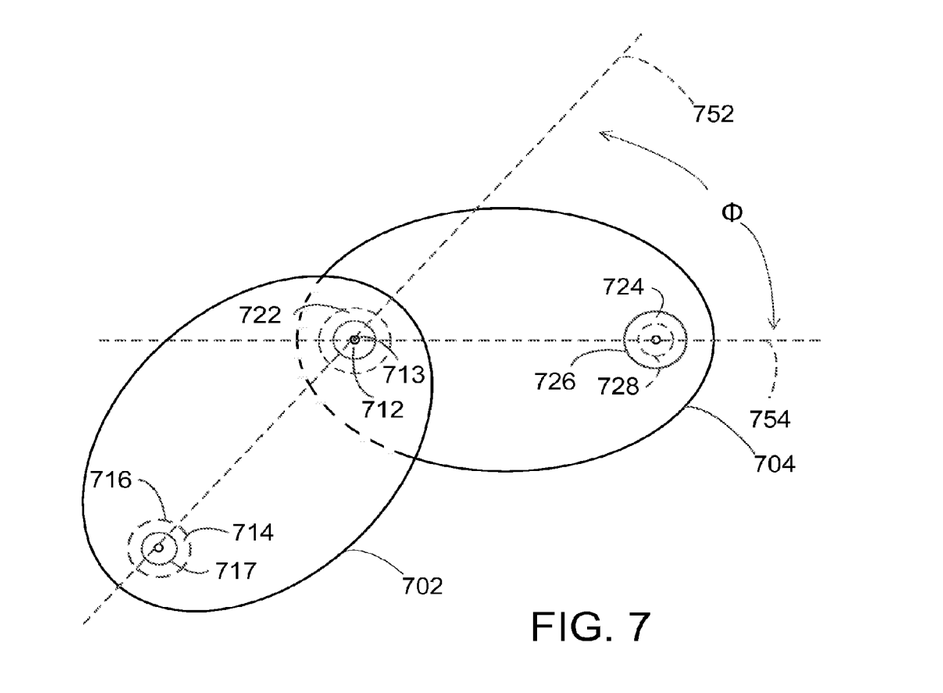
FIG. 7 is a schematic diagram of a light collector that includes stacked slab light guides with elliptical perimeters, and tilted with respect to each other.

FIG. 7 illustrates a representative example light collection system that includes stacked elliptical slab light guides 702, 704. The slab light guide 702 has a specimen aperture 712 situated at a first focus 713 and a truncated conical reflector 714 at a second focus. The truncated reflector 714 has a first diameter 716 and a second diameter 717 so that lateral light flux is reflected out of the page as shown in FIG. 7. The slab light guide 704 has a first conical reflector 722 having an apex situated above a first focus of the second slab light guide 704 and below the first focus 713 of the first slab light guide 702. Thus, the conical reflector 722 is configured to reflect a transmitted light flux towards a truncated conical reflector 724 situated at a second focus of the second slab light guide 704. The conical reflector has an upper diameter 726 that is larger than a lower diameter 728 and is thus configured to reflect a light flux into the plane of the page as shown in FIG. 7.

The slab light guide 702 has a focus-to-focus axis 752 and the slab light guide 704 has a focus-to-focus axis 754 that are at an angle φ with respect to each other. This angle can range from 0 degrees to 360 degrees and can be selected as convenient. Alternatively, the slabs can share a pivot at the second focal point (cf. FIG. 3) and use rotation between the slabs to facilitate access to the specimen.

Additional slab light guides can be similarly stacked in a manner similar to that shown in FIG. 7 so that trans, epi, and lateral light fluxes are directed to a single reflector, to multiple reflectors situated on a common axis or different axes, and light fluxes can be directed out of the slab light guides along a direction in which an incident light flux is received or an opposite direction. A conical reflective surface through which an incident light flux passes to reach a specimen can be provided with a dichroic coating so that incident flux in a first wavelength range is transmitted, and a multiphoton (or other fluorescent) light flux is reflected. Slab light guides having parabolic sections can be similarly stacked, or combination of slab light guides with parabolic and elliptical sections can be used.

Figure 8:
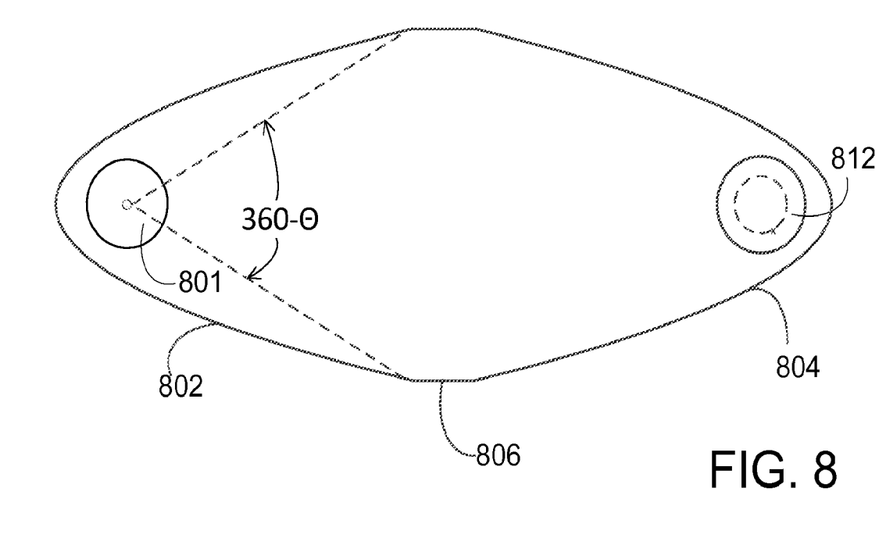
FIG. 8 is a plan view of a slab light guide light collector that includes two elliptical sections joined by section defined by line segments.

FIG. 8 illustrates a slab light guide that includes first and second parabolic or elliptical sections 802, 804 and intervening section 806 that can be tapered or untapered either in slab thickness or width. A sample recess 801 is situated at a focus of the first section 802, and the first section subtends an azimuthal angle 360-θΘ with respect to the focus (and the sample volume). A conical or other reflector 812 is situated at a focus of the second section 804, and the sections 802, 804 need not have the same focal length or ellipticity. As is apparent from FIG. 8, a slab light guide light collector is generally configured to collect light over a range of azimuthal angles up to 45 degrees, 90, degrees, 180 degrees, and approaching 360 degrees, i.e., Θ can approach 0.

Figure 10:
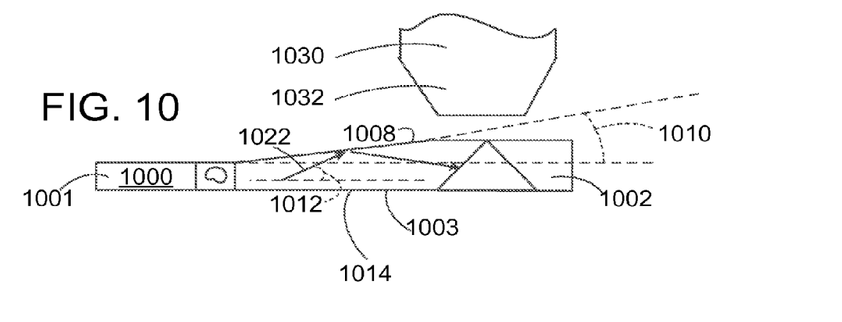
FIG. 10 is a sectional view of a slab light guide having a tapered section and an external tapered light guide placed so as to receive a light flux from the slab light guide.

FIG. 10 illustrates a slab light guide 1000 having untapered sections 1001, 1002 and a tapered section 1003. A top surface 1008 of the tapered section 1003 has a taper angle 1010 (α) with respect to an untapered rear surface 1014. Radiation propagating along a direction 1022 at an angle 1012 (β) with respect to the rear surface 1014 propagates at an angle of −β+2α with respect to the surface 1014 after reflection by the top surface 1008, so that an angular spread of light propagation within the slab light guide can be reduced. One or both of top and rear surfaces can be tapered, and all or just one or more selected portions of the light guide can be tapered. Alternatively or in addition, a cylindrical output light guide 1030 substantially along the axis of conic reflector 1014 having a tapered section 1032 can be provided, and it may contact the slab or simply be proximate.

Figure 11A:
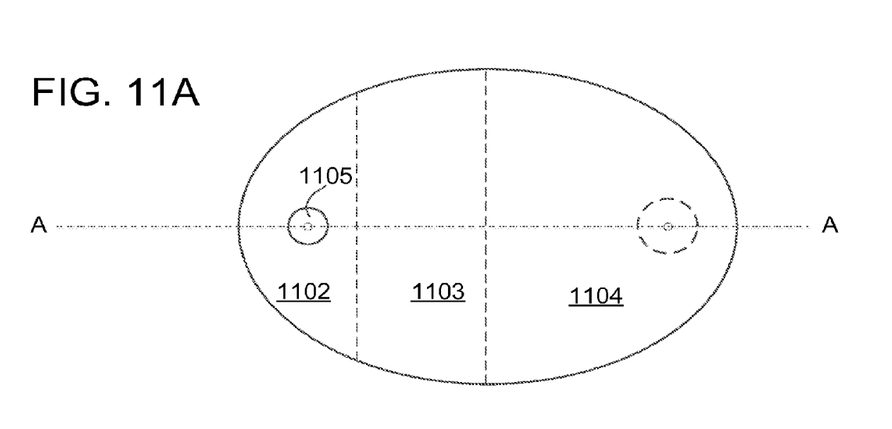
FIGS. 11A-11B are plan and sectional views, respectively, of a non-planar elliptical slab light guide.
Figure 11B:
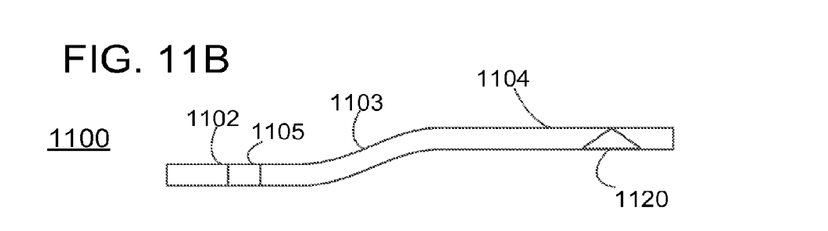

With reference to FIGS. 11A-11B, an elliptical light guide 1100 that is bent or otherwise configured to be non-planar includes a first section 1102 that includes a specimen aperture 1105, a second (transition) section 1103, and a third (light output) section 1104 that can include a conical reflector 1120. Any of the sections can be tapered, and thicknesses can be selected as convenient.

Figure 12:
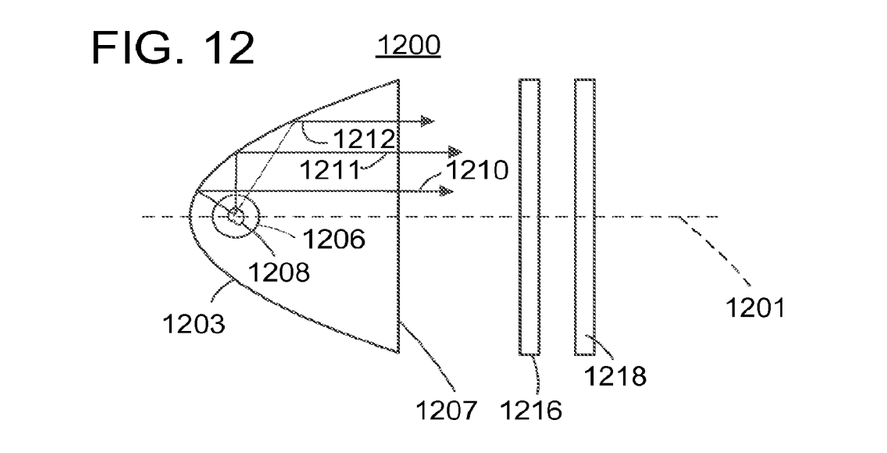
FIG. 12 is a plan view of a slab light guide having a parabolic perimeter.

FIG. 12 illustrates a truncated parabolic slab light guide 1200 that is truncated at a surface 1207 and has a parabolic perimeter 1203. A specimen 1208 can be situated in a specimen recess 1206 that is situated at a focus of the parabolic perimeter 1203. Representative propagation paths 1210, 1211, 1212 extend from the specimen 1208 to the surface 1207. Because these propagation paths from the specimen 1208 are substantially collimated at the surface 1207, a cylindrical lens 1216 can be situated so as to direct flux to a detector such as a linear array detector 1218. In other examples, a spherical lens, minor, or other collection optics can be used. In addition, although not shown in FIG. 12, the surface 1207 can be shaped so as to form a cylindrical lens element, or include a surface that is tilted with respect to an axis 1201 so that flux propagating along the directions 1210-1212 is reflected so as to propagate along an axis perpendicular to the axis 1201 and to a plane parallel to slab light guide top or bottom surfaces. Recess 1206 may be either curved or mirrored on a portion of the right face to preserve collimation.

Figure 13:
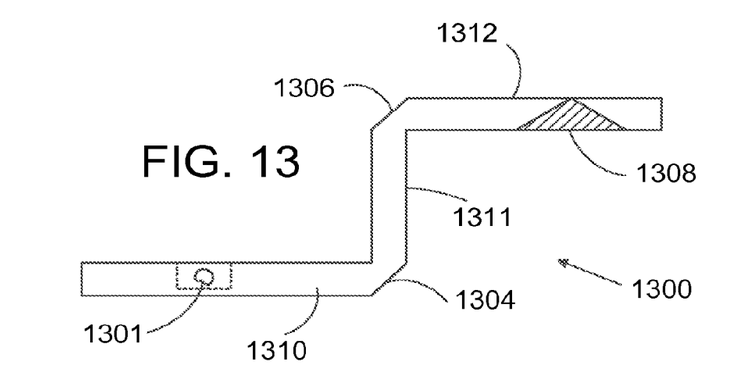
FIG. 13 is a sectional view of a folded slab light guide.

FIG. 13 illustrates a slab light guide 1300 that is folded with two 45 degree reflecting surfaces 1304, 1306 that can be provided with metallic or dielectric coatings. A reflector 1308 is situated to direct an emission flux from a specimen 1301 out of the slab light guide 1300. In the example FIG. 13, slab sections 1310-1312 have a common thickness, but different thicknesses can be used, and one or more of the sections 1310-1312 can be tapered in the plane of FIG. 13 or normal to the plane of FIG. 13. In other examples, additional folds can be provided so as to direct an emission flux in a direction that is out of the plane of FIG. 13.

Figure 14:
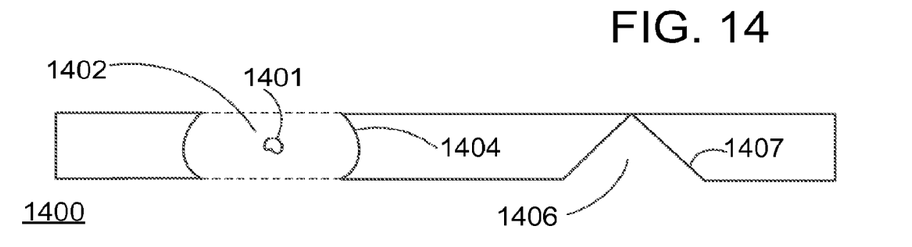
FIG. 14 is a sectional view of a slab light guide having a sample recess defined by curved side walls and a recess that defines reflective surfaces configured to direct a light flux out of the slab light guide.
Figure 15:
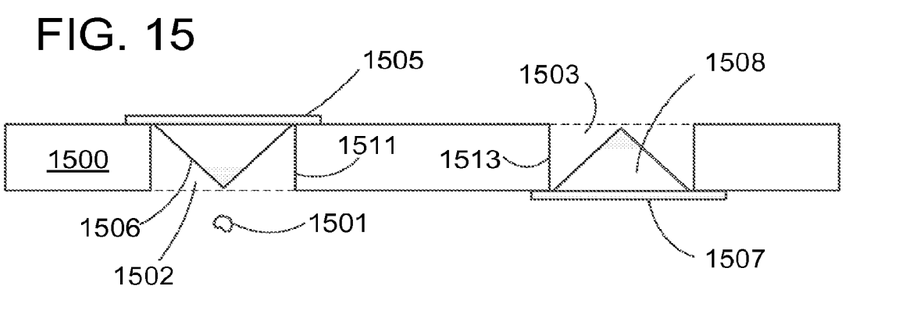
FIG. 15 is a sectional view of a slab light guide that includes recesses for conical prisms.

FIG. 14 illustrates a slab light guide 1400 have a specimen 1401 situated in a recess 1402 defined by a wall 1404 having a curvature selected to enhance coupling into the light guide. An indentation 1406 in the light guide 1400 defines a reflective surface 1407 that directs light flux from the specimen out of the light guide 1400. FIG. 15 illustrates a slab light guide 1500 that includes cavities 1502, 1503 that are configured to receive conical reflectors 1506, 1508, respectively. Respective support plates 1505, 1507 are provided to which the reflectors 1506, 1508 are secured. Light from a specimen 1501 can be directed into the slab light guide 1500 by the reflector 1506 and out of the slab light guide 1500 by the reflector 1506. As shown in FIG. 15, walls 1511, 1513 of the cavities 1502, 1503 are cylindrical, but one or both of these walls can be provided with other shapes for collimation, focusing, or other purpose. Reflector surfaces 1506,1508 can have parabolic or other complex profiles to enhance efficiency.

Figure 16:
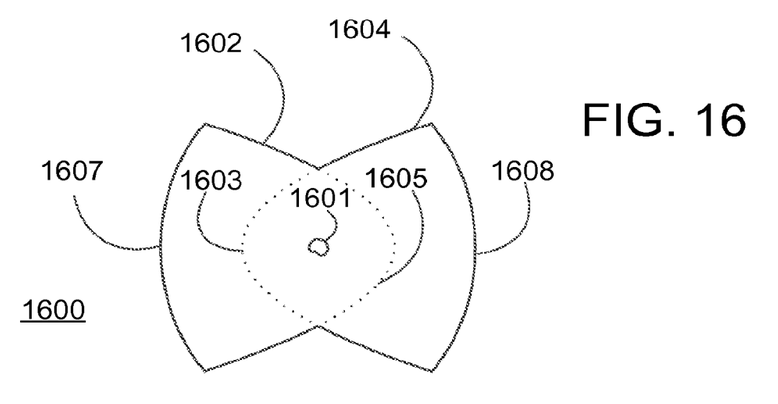
FIG. 16 is a plan view of a slab light guide that includes two parabolic sections sharing a common focus.

FIG. 16 illustrates a light guide 1600 that includes first and second parabolic sections 1602, 1604 that share a common focus at which a specimen 1601 can be situated. For purposes of illustration, corresponding parabolas 1603, 1605 are shown in dashed lines. Output surfaces 1607, 1608 are shown as curved to provide focusing of light collimated from the parabolic sections 1602, 1604, respectively, but planar surfaces or other surface curvatures can be provided. In this example, light flux that reaches a parabolic surface is directed away from the specimen and thus is not absorbed or scattered by passage into or through the specimen.

In some examples described above, elliptical or parabolic light guide perimeters are used, but in other examples, circular, arcuate, or other curved perimeters can be used to suitably direct light fluxes. In addition, such curves can be piece-wise approximated with one or more curve sections or straight line sections. The illustrated slab light guides are defined by opposing, parallel, planar surfaces, but in other examples, tapered slab light guides can be used having opposing surfaces which are tilted with respect to each other. In addition, the slab light guides need not be substantially planar but can have curved, bent, twisted, or other plane parallel or curved surfaces. It is convenient to provide conical or other reflectors that are situated entirely within a slab light guide, but in some examples, such reflectors can extend beyond the slab light guide. The examples above are for purposes of illustration, and we claim all that is encompassed by the appended claims.

I claim:

1. A light collector, comprising:
a slab light guide having an elliptical cross section defined by a first planar elliptical surface and a second planar elliptical surface opposite the first planar elliptical surface, wherein a first axis between a first focus and a second focus of a first planar elliptical surface and a second axis between a first focus and a second focus of the second planar elliptical surface are situated in the first planar elliptical surface and the second planar elliptical surface, respectively, the slab light guide situated to direct light via multiple reflections and defining a relief volume situated between the first focus of the first planar elliptical surface and the first focus of the second planar elliptical surface and configured to receive a specimen, the relief volume of the slab light guide bounded by at least one transmissive optical surface that directs received emission from the specimen in the relief volume into the slab light guide, the slab light guide further including a perimeter surface that couples the first planar elliptical surface and the second planar elliptical surface and configured to reflect the received emission propagating within the slab light guide to an output coupling region situated between a second focus of the first planar elliptical surface and a second focus of the second planar elliptical surface.

2. The light collector of claim 1, wherein the slab light guide is a hollow slab light guide.

3. The light collector of claim 1, wherein the slab light guide is a solid slab light guide.

4. The light collector of claim 1, wherein the first planar elliptical surface and the second planar elliptical surface are tilted with respect to each other so as to define a tapered slab light guide.

5. The light collector of claim 1, wherein the first planar elliptical surface and the second planar elliptical surface are substantially parallel.

6. The light collector of claim 5, further comprising an output reflector situated between the first planar elliptical surface and the second planar elliptical surface that define the slab light guide and at the second focus of the elliptical perimeter surface, the reflector situated to direct emission propagating within the slab light guide so as to exit the slab light guide through at least one of the opposing surfaces.

7. The light collector of claim 6, wherein the output reflector has a conical reflective surface.

8. The light collector of claim 1, further comprising a first reflective coating situated on the first planar elliptical surface and a second reflective coating situated on the second planar elliptical surface.

9. An apparatus, comprising:
a first slab light guide having a specimen volume, the first slab light guide defined by planar exterior surfaces having respective elliptical perimeter portions so as to guide light propagating in the first slab light guide by multiple reflections; and
a reflective surface situated between the planar exterior surfaces of the first slab light guide, wherein the elliptical perimeter portions of the planar exterior surfaces of the first slab light guide are configured so as to direct light flux received into the slab volume from the specimen volume to the reflective surface, and further wherein the reflective surface is configured to reflect the received light flux so as to exit the first slab light guide in a direction that is perpendicular to at least one of the planar exterior surfaces that define the slab light guide.

10. The apparatus of claim 9, wherein a perimeter surface of the first slab light guide includes an elliptical section and the specimen volume and reflective surface are situated at first and second focal points of the elliptical section.

11. The apparatus of claim 9, wherein the perimeter surface of the first slab light guide includes a tapered portion and an elliptical portion.

12. The apparatus of claim 9, wherein the first slab light guide includes reflective coatings on opposing slab surfaces.

13. An apparatus, comprising:
a first slab light guide having a specimen volume;
a reflective surface situated between exterior surfaces of the first slab light guide, wherein a perimeter surface of the first slab light guide is configured so as to direct light flux received into the slab volume from the specimen volume to the reflective surface, and further wherein the reflective surface is configured to reflect the received light flux so as to exit the first slab light guide, wherein the perimeter surface of the first slab light guide includes an elliptical section and the specimen volume and reflective surface are situated at first and second focal points of the elliptical section; and
a second slab light guide that includes first and second reflective surfaces at least partially situated between exterior surfaces of the second slab light guide, and situated with respect to the first slab light guide so that a light flux from the specimen volume of the first slab light guide is at least partially received by the first reflective surface and directed by the first reflective surface of the second slab light guide and the second slab light guide to the second reflective surface of the second slab light guide.

14. The apparatus of claim 13, wherein the second slab light guide has a perimeter corresponding to an elliptical section, and the first and second reflective surfaces are defined by conical surfaces at first and second focal points of the elliptical section.

15. The apparatus of claim 14, wherein a first axis that extends between the first and second focal points of the first slab light guide and a second axis that extends between the first and second focal points of the second slab light guide define an angle of between 10 degrees and 180 degrees.

16. An apparatus, comprising:
a first slab light guide having a specimen volume;
a reflective surface situated between exterior surfaces of the first slab light guide, wherein a perimeter surface of the first slab light guide is configured so as to direct light flux received into the slab volume from the specimen volume to the reflective surface, and further wherein the reflective surface is configured to reflect the received light flux so as to exit the first slab light guide; and
a second slab light guide that includes first and second reflective surfaces at least partially situated between exterior surfaces of the second slab light guide, and situated with respect to the first slab light guide so that a light flux from the specimen volume of the first slab light guide is at least partially received by the first reflective surface and directed by the first reflective surface and the second slab light guide to the second reflective surface of the second slab light guide.

17. A method, comprising:
exciting a specimen so as to produce emission from the specimen;

collecting at least a portion of laterally propagating emission from the specimen by situating the specimen in an aperture that extends between opposing surfaces of a slab light guide so as to propagate within the slab light guide by multiple internal reflections; and directing at least a portion of the laterally propagating emission out of the slab light guide in a direction perpendicular to the opposing surfaces of the slab light guide with a reflective surface situated within the slab light guide.

18. The method of claim 17, wherein the slab light guide is a solid slab light guide, and further comprising directing at least a portion of the laterally propagating emission out of the solid slab light guide with a reflective surface situated within the solid slab light guide.

19. The method of claim 17, wherein the slab light guide is a solid slab light guide, and a perimeter of the solid slab light guide includes a parabolic or an elliptical section.

20. The method of claim 17, further comprising directing at least a portion of the collected lateral emission to an output surface with a tapered light guide.

21. The method of claim 20, further comprising directing at least a portion of the collected lateral emission to a focusing element configured to concentrate the collected lateral emission at a location outside of the slab light guide.

22. The method of claim 21, wherein the focusing element is a cylindrical lens formed on an output surface of the slab light guide.

23. The method of claim 17, wherein emission from the specimen is produced by excitation with an optical beam.

24. A method, comprising:

exciting a specimen so as to produce emission from the specimen;

collecting at least a portion of laterally propagating emission from the specimen by situating the specimen in an aperture that extends between opposing surfaces of a slab light guide so as to propagate within the slab light guide; and collecting at least a portion of a transmitted flux with a second slab light guide.

25. The method of claim 24, further comprising directing the portion of the transmitted flux collected by the second slab light guide with a reflective surface so as to propagate within the second slab light guide.

26. The method of claim 25, wherein the reflective surface has a profile that corresponds to a surface of rotation.

27. The method of claim 26, wherein the surface of rotation is a parabolic surface of rotation.

* * * * *